United States Patent [19]

Voigt

[11] Patent Number: 4,514,341

[45] Date of Patent: Apr. 30, 1985

[54] STORAGE STABLE NITROGLYCERIN

[75] Inventor: H. William Voigt, Wharton, N.J.

[73] Assignee: The United States of America as represented by the Secretary of the Army, Washington, D.C.

[21] Appl. No.: 601,878

[22] Filed: Apr. 19, 1984

[51] Int. Cl.³ .............................................. C07C 77/02
[52] U.S. Cl. ...................................... 260/467; 149/101
[58] Field of Search ......................... 260/467; 149/101

[56] References Cited

U.S. PATENT DOCUMENTS 3,882,784  5/1975  Nauflett et al. ......................... 149/2
3,907,907  9/1975  Frankel et al. .................... 149/88 X
3,965,676  6/1976  Schaffling ......................... 149/15 X

FOREIGN PATENT DOCUMENTS 1214208  4/1966  Fed. Rep. of Germany ...... 260/467
1324498  3/1963  France ................................ 260/467

Primary Examiner—Leland A. Sebastian
Attorney, Agent, or Firm—Anthony T. Lane; Robert P. Gibson; Edward F. Costigan

[57] ABSTRACT

A liquid epoxy plasticizer is added to a bulk quantity of nitroglycerin to render the same stable in storage and to enhance its safety relative explosion.

4 Claims, No Drawings

STORAGE STABLE NITROGLYCERIN

GOVERNMENTAL INTEREST

The invention described herein may be maufactured, used and licensed by or for the Government for Governmental purposes without payment to me of any royalty thereon.

BACKGROUND OF INVENTION

1. Field of Use

This invention relates to a method of rendering nitroglycerin or glyceryl trinitrate stable in storage.

More particularly, this invention relates to additives for use in a process of treating nitroglycerin to make the same stable on storage.

2. Description of Prior Art

Nitroglycerin is known to decompose on storage due to the production of acidic by-products resulting in an increase in temperature from decomposition leading to instability. Nitroglycerin at a temperature above 50° C. is considered dangerous. Heat caused by decomposition must be removed quickly or it may lead to an explosion. This is particularly dangerous where a large batch may be held in a storage tank prior to transporting it for use in double and triple base propellant mixes. Hydrolysis and acidification or "souring" of the raw nitroglycerin occurs in storage and is the first stage in its decomposition, which is then accelerated by by-products such as NO and $NO_2$ and the presence of water. The development of acidity accelerates further decomposition of the nitroglycerin. It has been found that when 0.3 gms of nitroglycerin with 5% $HNO_3$ added thereto was sealed and stored at 41° C. an explosion occurred within 320 minutes although the sample temperature rose by only a few degrees as a result of the catalytic effect of the nitric acid on the nitroglycerin. This is especially dangerous where large amounts of nitroglycerin are involved. Further, the resultant nitroglycerin is of poor heat stability due to decomposition products and is unsatisfactory for propellant use.

SUMMARY OF INVENTION

It is therefore an object of this invention to provide nitroglycerin having improved storage stability relative to safety.

Another object is to provide a method for treating raw nitroglycerin with additives to eliminate undesirable heat storage instability.

Other objects and features of this invention will become apparent as the invention becomes better understood from a reading of the following detailed specification.

In general, a liquid epoxy plasticizer is added to the nitroglycerin to increase the stability of the same during storage. It has been found that the plasticizer takes up the acidic decomposition products as they are formed in the nitroglycerin. In this manner, the nitric acid which increases the instability of nitroglycerin is removed and there is a lesser danger of explosion.

The liquid epoxy plasticizers which are soluble in nitroglycerin and insoluble in water and may be used in this treatment include the following, viz.

1. A liquid epoxy resin being the condensation product of epichlorohydrin and bisphenol A having an epoxy equivalent of 180–195, Epon 828, product of Shell Chemical Co.

2. Pentaerythrital tetraepoxy stearate, X-45, product of Celanese Chemical Co., Dallas, Tex.

3. Epoxidized soybean oil, Epoxy Gen 90, product of General Mills or Epoxol 7-4, product of American Chemical Services, Griffith, Ind., or Plastolein 9232, product of Emery Industries, Cincinnati, Ohio.

4. Glyceryl triepoxy acetoxy stearate, Estynox 308, product of Cas Chem, Bayonne, N.J.

5. Epoxidized linseed oil, Epoxol 9-5, product of American Chemical Services, Griffith, Ind.

6. Butyl ester of epoxidized linseed oil, Epoxol 8-2B, product of American Chemical Services, Griffith, Ind.

7. Epoxidized octyl tallate.

The above liquid epoxy plasticizers improve heat stability of the nitroglycerin by preventing the development of acidic decomposition at the outset. They are liquid, soluble reagents which are mixed with the nitroglycerin, without curing agents, and stabilize the nitroglycerin for storage with an enhanced degree of safety. Note should be taken that the epoxy plasticizer is not removed from the nitroglycerin, either in its storage or in its subsequent use in propellant mixes.

The liquid epoxy plasticizers may be added to the nitroglycerin in an amount between 0.25 to 5.0 weight percent without interfering with the basic function of the nitroglycerin. The preferred amount of polymer added to the nitroglycerin is about 0.5 to 1.0 percent by weight.

EXAMPLE 1

1 gm of Epoxol 9-5 was added to 100 gms of nitroglycerin with stirring. The liquid epoxy platicizer was completely miscible in the nitroglycerin.

EXAMPLE 2

In this case 2 gms of Epoxol 9-5 was added to 100 gms of nitroglycerin. The liquid epoxy plasticizer was uniformly soluble in the nitroglycerin without any settling with only slight stirring used.

The military specification for nitroglycerine requires that a potassium iodide (KI) test be conducted to allow its use in propellant manufacture. If the KI value is less than 10 minutes for a color change of the KI paper, the nitroglycerin is considered unstable due to the onset of decomposition. The test is conducted for a maximum period of 15 minutes, and a 10–15 minutes value is specified for satisfactory nitroglycerin.

TABLE 1

| | KI Test | |
|---|---|---|
| Material | | Color Change in minutes |
| (1) Raw nitroglycerin (Control) | | (1) 6 min. |
| (2) Nitroglycerin + 2 wt. % Epoxol 9-5 | | (2) 80+ min. |

Another useful measurement of the stability of an explosive is the Vacuum Stability Test. It is a measurement in mls of gas liberated due to decomposition of the nitroglycerin when subjected to 90° C. for a period of time.

Both the KI Test and the Vacuum Stability Test are described in "Standard Laboratory Procedures for Sensitivity, Brisance, and Stability of Explosives", Arthur J. Clear, Feltman Research Laboratories, Picatinny Arsenal, Dover, N.J., April 1970. For safety in military use, the maximum amount of gas to be evolved in a 40 hour period from a 5 gm sample of propellant at 90° C.

should preferably be 0–2 ml gas (negligible) or 3–5 ml gas (slight). If the gassing is 6–10 ml gas (moderate) or 11+ ml gas (excessive), the propellant is considered unstable and unsatisfactory. However, when conducting the test on nitroglycerin per se a sample size below 5 grams is used.

TABLE 2

| Material | Vacuum Stability 90° C. | | |
|---|---|---|---|
|  | Amount | Time | Gas Evolved |
| Raw nitroglycerin (control) | 2.96 grams | 18 hrs. | 11 + ml (excessive) |
| Nitroglycerin + 1 wt % Epoxol 9-5 | 3.09 grams | 40 hrs. | 1.05 ml (negligible) |

What is claimed is:

1. In an improved nitroglycerin fluid which is stable for large bulk storage, the improvement consisting essentially of the incorporation in said nitroglycerin of a soluble liquid inert epoxy plasticizer selected from the group consisting of:
   A. The condensation product of epichlorohydrin and bisphenol A,
   B. Pentaerythritol tetraepoxy stearate,
   C. Epoxidized soybean oil,
   D. Glyceryl triepoxy acetoxy stearate,
   E. Epoxidized linseed oil,
   F. Butyl ester of epoxidized linseed oil, and
   G. Epoxidized octyl tallate said liquid plasticizer is present in an amount between about 0.24 and about 5.0 percent by weight.

2. The nitroglycerin of claim 1 wherein said liquid plasticizer is present in an amount between about 0.5 to about 1.0 percent by weight.

3. In an improved process of rendering a nitroglycerin fluid stable for large bulk storage, the improvement consisting essentially of dissolving a soluble inert liquid epoxy plasticizer in said nitroglycerin, said liquid plasticizer selected from the group consisting of
   A. The condensation product of epichlorohydrin and bisphenol A,
   B. Pentaerythritol tetraepoxy stearate,
   C. Epoxidized soybean oil,
   D. Glyceryl triepoxy acetoxy stearate,
   E. Epoxidized linseed oil,
   F. Butyl ester of epoxidized linseed oil, and
   G. Epoxidized octyl tallate said liquid plasticizer dissolved in an amount between about 0.25 and about 5.0 percent by weight.

4. In the process of claim 3 wherein said soluble liquid epoxy plasticizer is dissolved in an amount between about 0.5 and about 1.0 percent by weight.

* * * * *